(12) United States Patent
Dowling et al.

(10) Patent No.: US 9,440,013 B2
(45) Date of Patent: Sep. 13, 2016

(54) DEVICES, METHODS AND SYSTEMS FOR COUNTERPULSATION AND BLOOD FLOW CONDUIT CONNECTION

(71) Applicant: ABIOMED, INC., Danvers, MA (US)

(72) Inventors: Robert Dowling, Louisville, KY (US); Robert T.V. Kung, Andover, MA (US); Paul Spence, Louisville, KY (US); Thorsten Siess, Wurselen (DE); Gerd Spanier, Aachen (DE); Eric Gratz, Louisville, KY (US); Caitlyn Hastie, Billerica, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 14/522,383

(22) Filed: Oct. 23, 2014

(65) Prior Publication Data

US 2015/0265757 A1   Sep. 24, 2015

Related U.S. Application Data

(63) Continuation of application No. 14/238,391, filed as application No. PCT/US2012/050604 on Aug. 13, 2012, now abandoned.

(60) Provisional application No. 61/522,401, filed on Aug. 11, 2011.

(51) Int. Cl.
*A61N 1/362* (2006.01)
*A61M 1/10* (2006.01)
(Continued)

(52) U.S. Cl.
CPC .............. *A61M 1/1008* (2014.02); *A61B 17/11* (2013.01); *A61F 2/064* (2013.01); *A61M 1/107* (2013.01); *A61M 1/1032* (2014.02); *A61M 1/122* (2014.02); *A61M 1/3653* (2013.01); *A61M 25/0043* (2013.01); *A61M 25/0071* (2013.01); *A61M 25/0074* (2013.01); *A61B 2017/00884* (2013.01); *A61B 2017/1135* (2013.01);
(Continued)

(58) Field of Classification Search
CPC .................... A61B 17/11; A61B 2017/00884; A61B 2017/1135; A61F 2250/0026; A61F 2/0077; A61F 2/064; A61M 1/1008; A61M 1/1032; A61M 1/107; A61M 1/122; A61M 1/3653; A61M 2025/006; A61M 2206/10; A61M 25/0043; A61M 25/0071; A61M 25/00
See application file for complete search history.

(56) References Cited

U.S. PATENT DOCUMENTS 4,240,409 A * 12/1980 Robinson et al. .............. 600/16
4,573,576 A    3/1986 Krol
(Continued)

FOREIGN PATENT DOCUMENTS

WO    WO-2013023009    2/2013

OTHER PUBLICATIONS

International Search Report mailed Oct. 23, 2012 for PCT/US/1250604.
(Continued)

*Primary Examiner* — George Manuel
(74) *Attorney, Agent, or Firm* — Ropes & Gray LLP

(57) ABSTRACT

A blood flow conduit includes a first conduit portion defining a first portion of a lumen; and a second conduit portion defining a second portion of a lumen. At least one of the first or second conduit portions may include a tip portion and the other of the first or second conduit portions may include an enlarged area.

10 Claims, 9 Drawing Sheets

(51) Int. Cl.
*A61M 1/12* (2006.01)
*A61F 2/06* (2013.01)
*A61B 17/11* (2006.01)
*A61M 1/36* (2006.01)
*A61M 25/00* (2006.01)
*A61F 2/00* (2006.01)
*A61B 17/00* (2006.01)

(52) U.S. Cl.
CPC ..... *A61F 2/0077* (2013.01); *A61F 2250/0026* (2013.01); *A61M 2025/006* (2013.01); *A61M 2206/10* (2013.01)

(56) References Cited

U.S. PATENT DOCUMENTS

| | | |
|---|---|---|
| 5,084,064 A | 1/1992 | Barak et al. |
| 5,327,885 A | 7/1994 | Griffith |
| 6,050,975 A | 4/2000 | Poirier |
| 6,390,969 B1 | 5/2002 | Bolling et al. |
| 6,524,322 B1 | 2/2003 | Berreklouw |
| 2002/0095210 A1 | 7/2002 | Finnegan et al. |
| 2005/0119573 A1 | 6/2005 | Vilenkin et al. |
| 2006/0020242 A1 | 1/2006 | Yamazaki et al. |
| 2007/0208290 A1 | 9/2007 | Pecor et al. |
| 2009/0048663 A1 | 2/2009 | Greenberg |
| 2010/0280306 A1 | 11/2010 | Spence |
| 2010/0324667 A1 | 12/2010 | King |
| 2014/0316189 A1 | 10/2014 | Spence |

OTHER PUBLICATIONS

PCT International Search Report for International Application No. PCT/US12/66292, mailed Feb. 5, 2013 (3 pages).

* cited by examiner

DEVICES, METHODS AND SYSTEMS FOR COUNTERPULSATION AND BLOOD FLOW CONDUIT CONNECTION

CROSS REFERENCE TO RELATED APPLICATIONS

This application is a continuation of U.S. patent application Ser. No. 14/238,391, which was filed Feb. 11, 2014 as the United States National Stage of International Patent Application No. PCT/US2012/050604, filed Aug. 13, 2012, which claims the benefit of priority of U.S. Provisional Application Ser. No. 61/522,401, filed Aug. 11, 2011.

BACKGROUND

Counterpulsation is a well-recognized form of mechanical assistance for the heart. It is used in over 100,000 patients worldwide each year and many patients with short term cardiac dysfunction can be saved. Almost all of these patients currently undergo treatment with an Intra Aortic Balloon Pump (IABP) which is composed of a balloon attached to a catheter that resides in the patient's descending aorta and which is inflated and deflated to improve the heart's performance. The balloon catheter is usually inserted in a groin artery and the catheter is connected to a console which is placed beside the patient's bed. The console shuttles a light gas, such as Helium, through the narrow catheter into and out of the balloon. The balloon is timed to empty very quickly as the heart beats, which lowers the pressure inside the aorta and makes it easy for the heart to eject blood. When the heart relaxes, the balloon fills and blood is pushed through the arteries of the heart and the rest of the body. The combination of reduced work for the heart and improved blood flow to the heart have a very salutary effect on cardiac function.

Unfortunately for the patient, the catheter is inserted in the groin and he or she must remain supine in bed. This condition cannot be maintained indefinitely as the patient becomes weak from immobility. Also, infection sometimes travels up the catheter and into the blood stream, causing a serious condition.

SUMMARY

According to one aspect, a blood flow conduit includes a first conduit portion defining a first portion of a lumen and a second conduit portion defining a second portion of a lumen. At least one of the first or second conduit portions may include a tip portion and the other of the first or second conduit portions may include an enlarged area.

DETAILED DESCRIPTION

Figure 1:
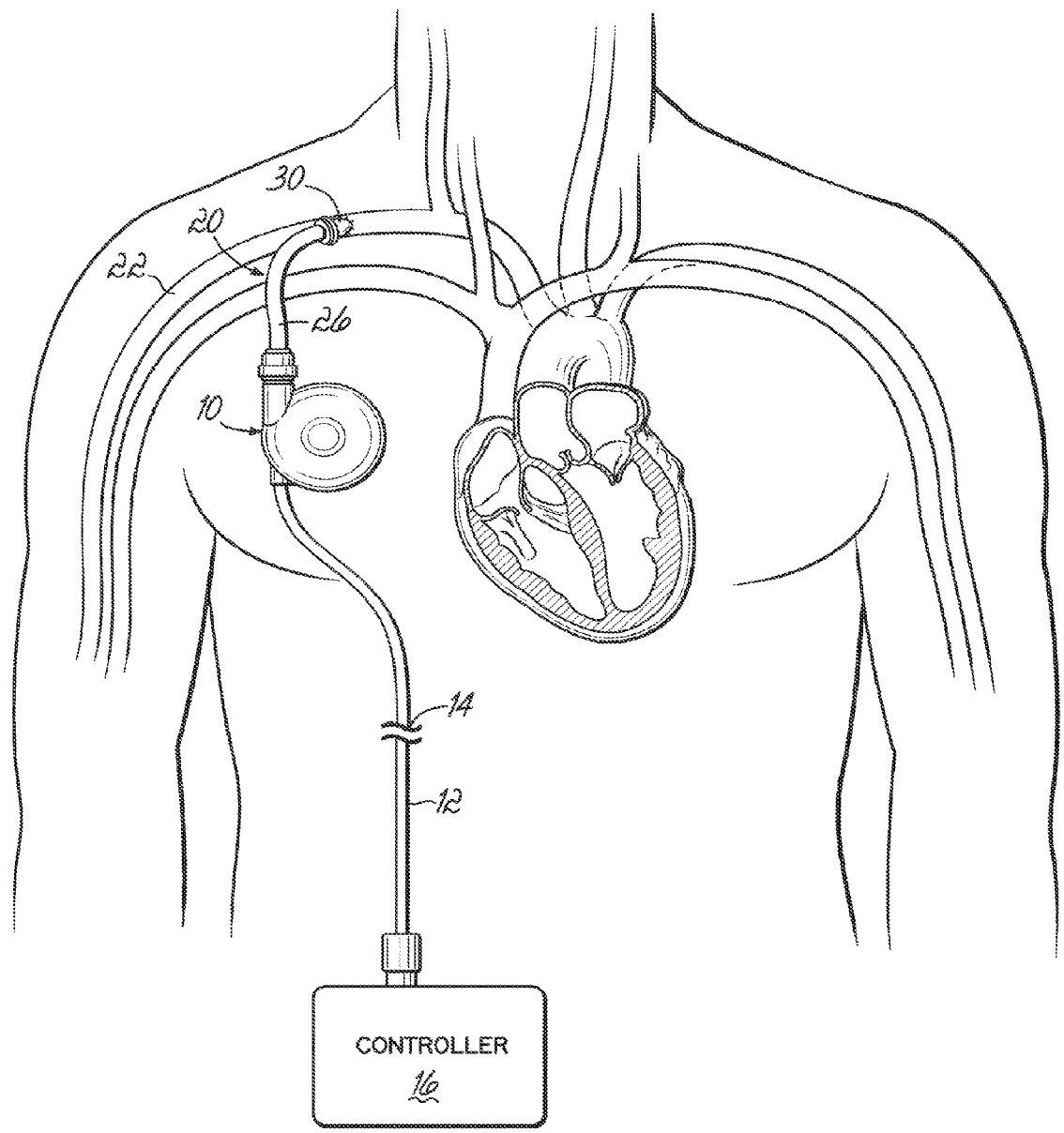
FIG. 1 is a schematic drawing of a patient with a counterpulsation system constructed according to some embodiments.

An alternative form of counterpulsation is shown in FIG. 1. Here a pump 10 is implanted in a pacemaker pocket on the patient's right side. Blood fills the pump 10 on one side and air or other fluid fills a sac or bladder (not shown) on the other side of the pump 10. An air drive line 12 is tunneled from the pacemaker pocket to a skin exit site 14, so the entire pump 10 is under the skin and can remain there chronically. After the driveline 12 exits the skin, it is attached to a small air drive unit 16 that controls shuttling of pressurized air in and out of the pump 10. A void in the pump 10 may be formed with the sac or bladder. The void fills with air as the heart beats (less cardiac work in ejecting blood) and empties to return blood into the circulation (more flow to the patient). The pump 10 is attached to the circulation with a conduit 20. The conduit 20 shuttles blood between the patient's circulatory system and the pump 10. This situation allows a patient to have chronic counterpulsation with full mobility. For a patient with severe and potentially non-reversible cardiac dysfunction, this is a great advantage as it is possible to live a relatively normal life—apart from the need to carry a small battery powered drive console 16.

As described, the blood is shuttled in and out of the pump 10 with a conduit 20 which is connected to the circulation. There are a number of considerations related to implantation and use of this conduit 20. First, almost every conduit has blood flowing in one direction, but this conduit 20 has blood alternating flow direction two times for each heart beat as the pump 10 fills and empties with each cardiac cycle. This creates a number of important issues which will be described. A second potential difficulty with a conduit in this situation is that it will typically be sewn to the subclavian artery 22 or axillary artery which is located beneath the clavicle and often quite deep, so it is technically difficult for a surgeon to suture the end of the conduit 20 to the artery 22.

The problem of a conduit with bidirectional flow relates to the responses of blood and tissues to the interfaces with synthetic materials and the response is dependent on the direction of blood flow. Many medical devices, such as blood pumps, are connected to the patient's circulation with artificial graft material such as polyester materials like Dacron® or expanded, porous Teflon® (ePTFE) that will promote tissue or ceil ingrowth. The inside of blood pumps are generally smooth and composed of metals or plastics, When blood flows from a smooth metal or plastic blood pump into a synthetic graft (such as polyester), the interface where the pump meets the conduit (plastic or metal to synthetic graft) is a stable junction and there tends to be little problem when blood flows forward through this junction.

Unfortunately, experience has shown that when blood instead flows from a synthetic graft such as polyester into a smooth surfaced blood pump, a deposit of blood elements including platelets and fibrin tends to deposit at the junction of the two materials—principally on the synthetic graft and overhanging the inflow to the pump. These deposits, especially platelets, tend to attract more blood elements and large and often fragile deposits occur at this junction. These deposits can break free from the junction and enter the blood pump and be sent through the patient's circulation. These deposits can flow anywhere, but if they arrive in an artery to the brain, a stroke can result. For this reason, many successful blood pumps employ a smooth synthetic conduit (such as silicone or urethane) for blood inflow into the pump.

The problem with counterpulsation is that blood is flowing in an alternating bi-directional manner. One solution would be to use a smooth silicone or urethane conduit which would create a stable junction between the pump and the conduit where the blood enters into the pump. This solves the problem at the inflow to the pump. However, when a silicone material is anastomosed (sewn) to an artery, the junction develops a heavy deposit of blood material (fibrin and platelets). So merely replacing the inflow conduit with a silicone surface is not satisfactory. It is tempting to merely have a silicone conduit and add a fabric extension, but this merely moves the problem that occurs at the junction of the rough textured surface of the graft and the pump to the junction between the graft and the silicone tube or cannula.

Figure 8:
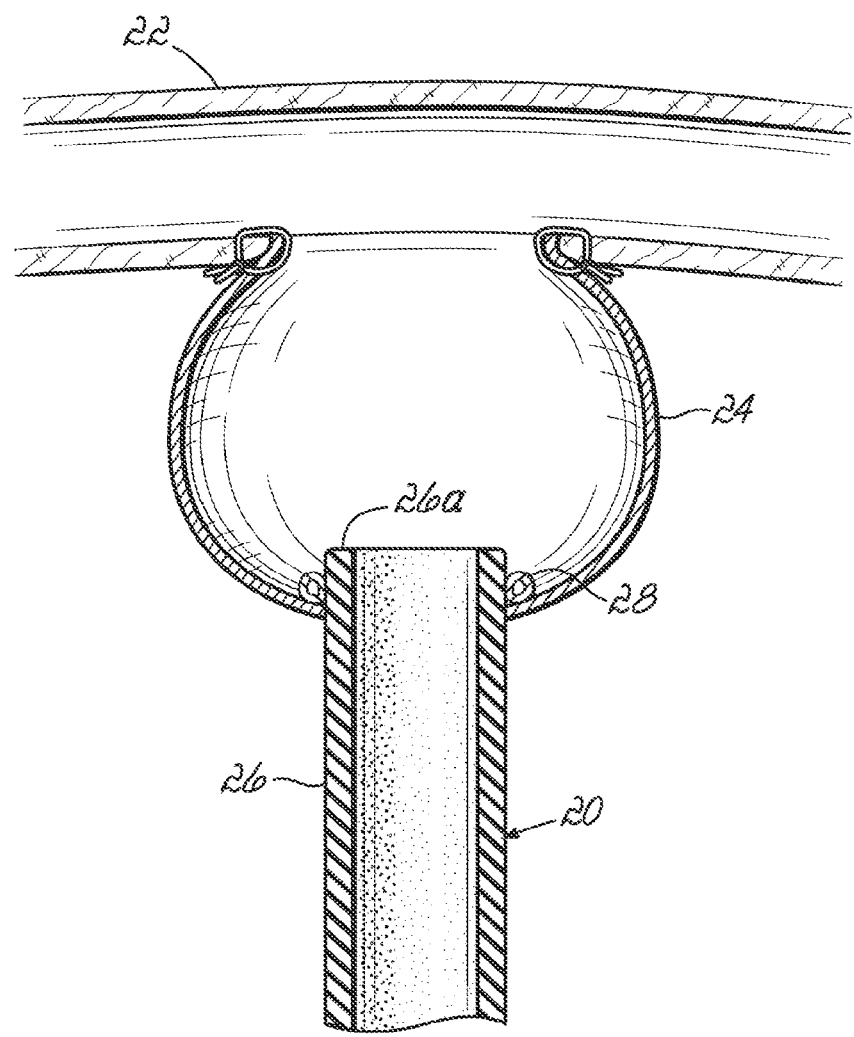
FIG. 8 is a cross-sectional view of a graft element attached to a blood flow conduit and an artery.

FIG. 8 shows one potential solution in a cross-sectional view. The subclavian artery 22 is shown at the top of the figure. A "bubble" or enlarged area 24 of Dacron®, Teflon® or other material is sewn to the artery 22. A silicone or other smooth material conduit portion 26 is connected to the other side of the enlarged area 24. Rather than a direct junction, a special interface is created. The smooth silicone surface portion 26 extends with a tip portion 26a several millimeters inside the enlarged area 24 of fabric or other material. The walls of the silicone tip portion 26a do not contact the fabric or material of the enlarged area or bubble 24. This avoids a silicone-to-fabric (or smooth-to-rough) point of contact.

Heart valves have been constructed with arrangements to avoid tissue ingrowth into the valve by creating an elevation—so that there is not a continuous connection between the fabric surface and the smooth surface. This elevation prevents tissue from growing over into junction point and creating a point where platelets and fibrin are deposited. The use of a small washer of material may also be of use. FIG. 8 shows a small washer 28 around the base of the tip 26a that may help arrest the attachment of blood elements.

Figure 9:
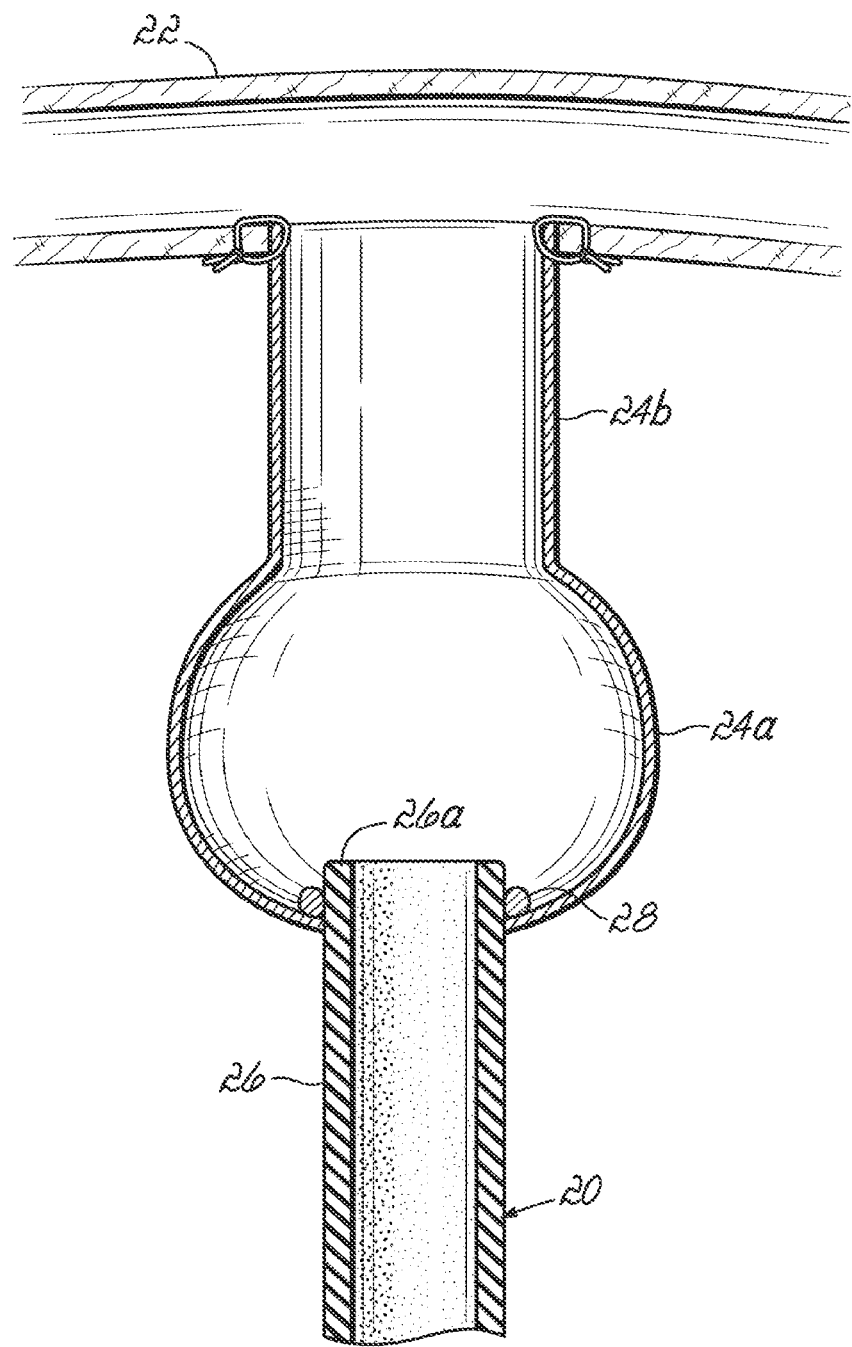
FIG. 9 is a cross-sectional view of a graft element attached to a blood flow conduit and an artery.

FIG. 9 shows that this arrangement of the "bubble" or enlarged area 24a of graft material is located away from the anastomosis. Specifically, enlarged area 24a is coupled to or includes an extension 24b that is anastomosed to the artery 22. Other features may be as described previously.

Figure 10A:
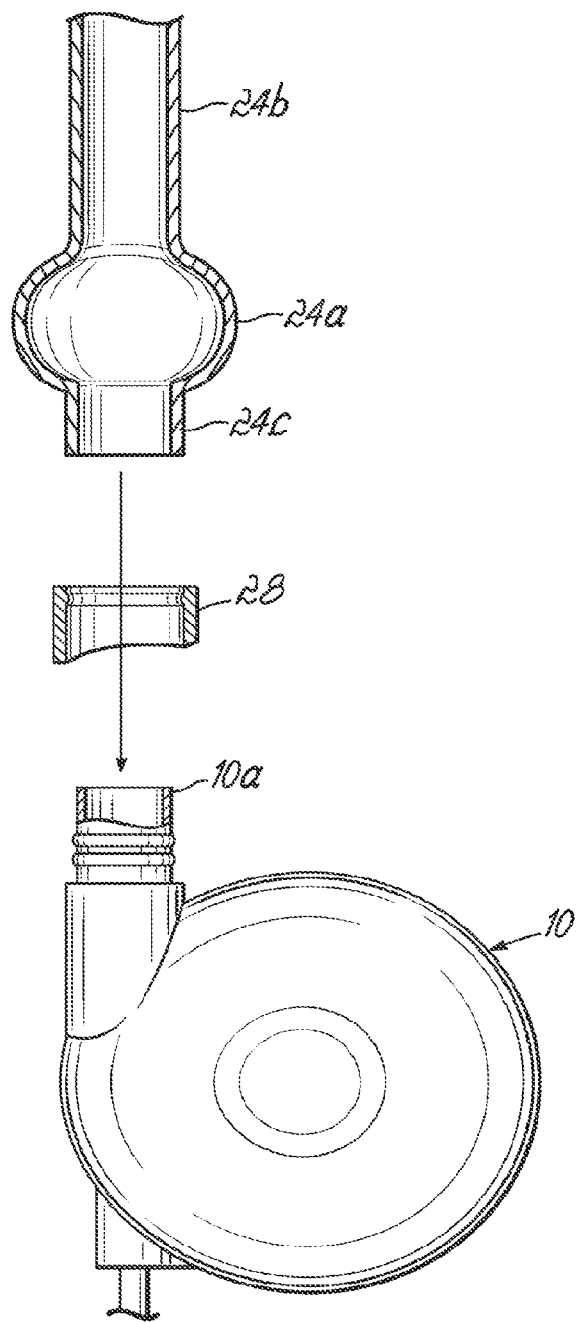
FIG. 10A is a disassembled view, in partial cross-section, illustrating the graft element of FIG. 9 and a blood pump.
Figure 10B:
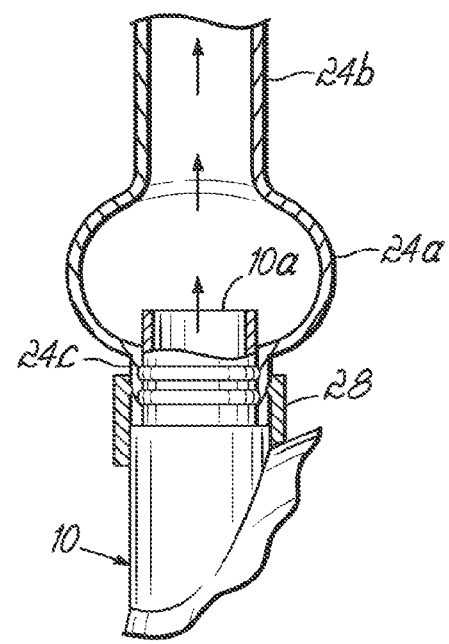
FIG. 10B is an assembled view, in partial cross-section, illustrating the graft element of FIG. 9 and a blood pump.

FIGS. 10A and 10B show a similar arrangement can be made at the junction of the pump 10. Here, the plastic, metal or other smooth surfaced junction or tip portion 10a of the pump 10 is separated from the rough surface of the enlarged graft material by a bubble interface 24a. An extension 24b of the graft material is sewn to the artery 22 (FIG. 9) as previously described. Another extension 24c on the opposite end may facilitate connection to the pump interface or tip portion 10a, along with a suitable connector 28. The junction or interface 10a, which serves as an inlet/outlet port that extends into, but does normally not contact, the graft material 24a in use.

These devices with bubbles or enlargements could be made In one piece. As described previously, the subclavian artery 22 is located fairly deep and the incision is small. So a surgeon who is trying to sew a graft with a bubble or enlargement on it is working in a deep hole. The bubble or enlargement on the end of a graft obscures his view of the artery. It would be useful to avoid this problem and also satisfy the need for maintaining the arrangement where the smooth and rough surfaces are not in direct linear contact.

Figure 2:
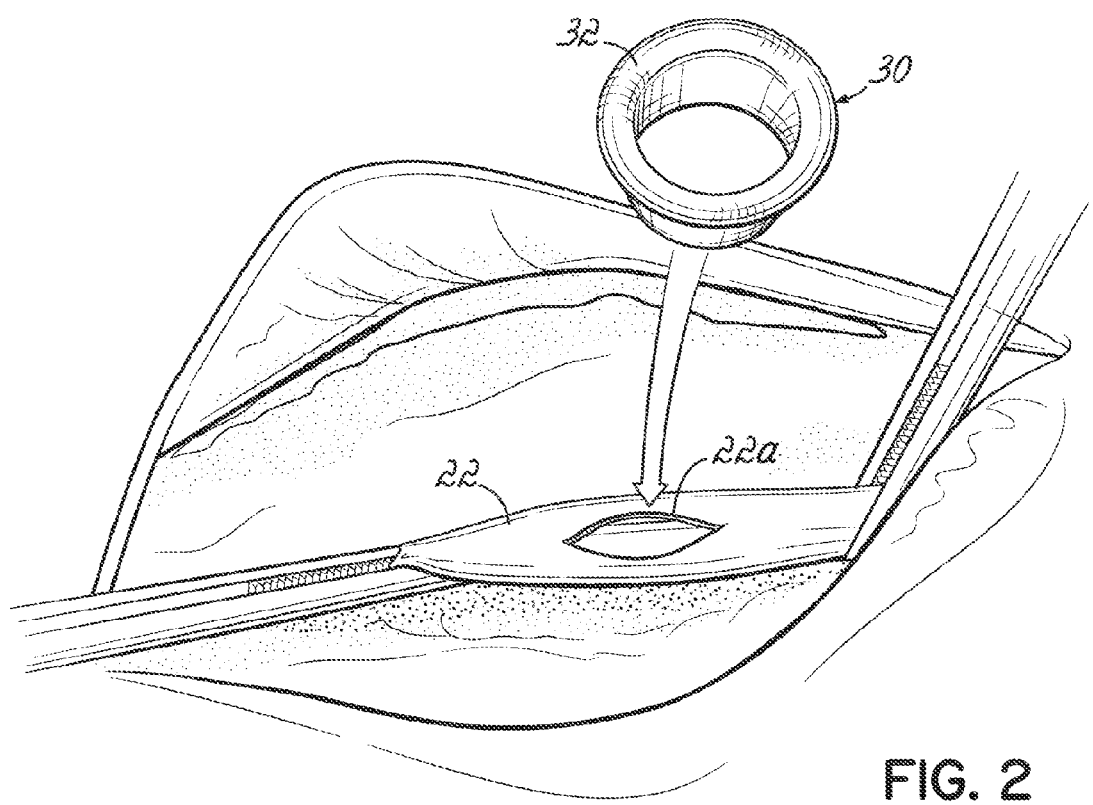
FIG. 2 is a perspective view illustrating a graft element of FIG. 1 being directed toward an artery for attachment purposes.
Figure 3:
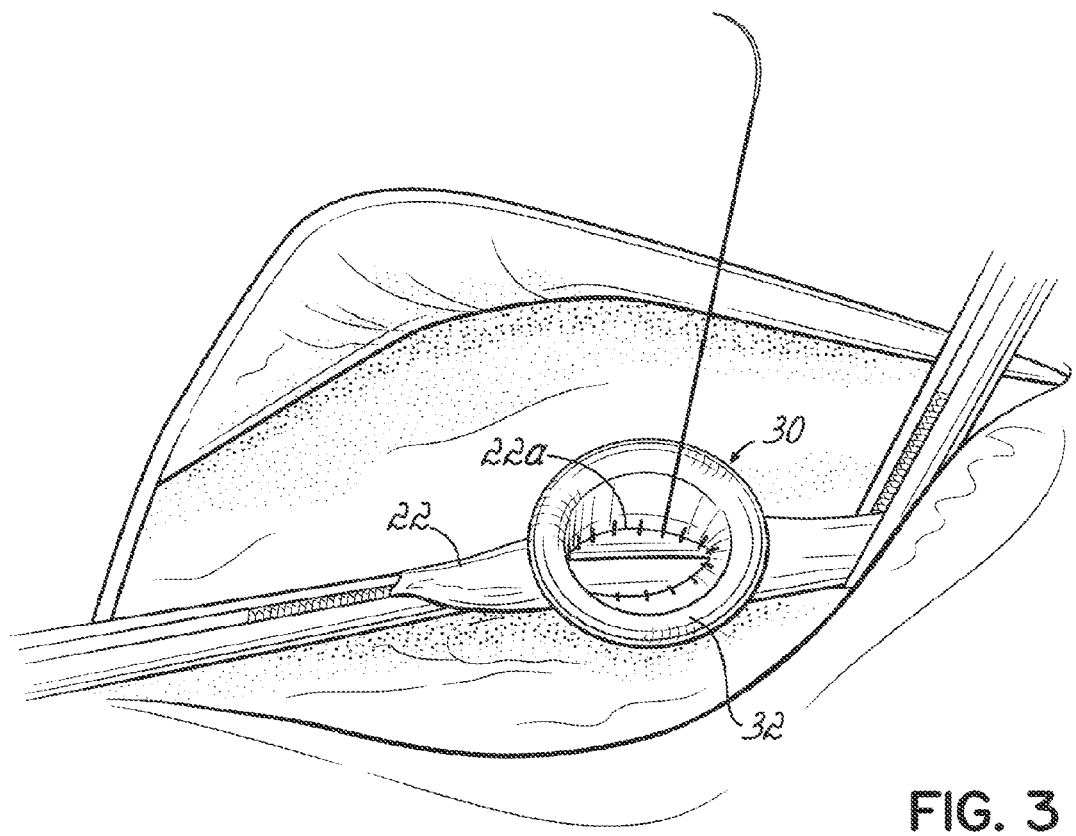
FIG. 3 is a perspective view similar to FIG. 2 and illustrating the graft element being sewn to the artery.

Such a solution is shown in FIGS. 2 and 3. Here, a graft element form from material such as described above is sewn to the artery. The graft element 30 has a flange 32 at one end. The element 30 is small and easy to move around, so does not obscure the view of the surgeon. FIG. 3 shows that it is easy to sew this element 30 around an opening 22a on the artery 22.

Figure 4:
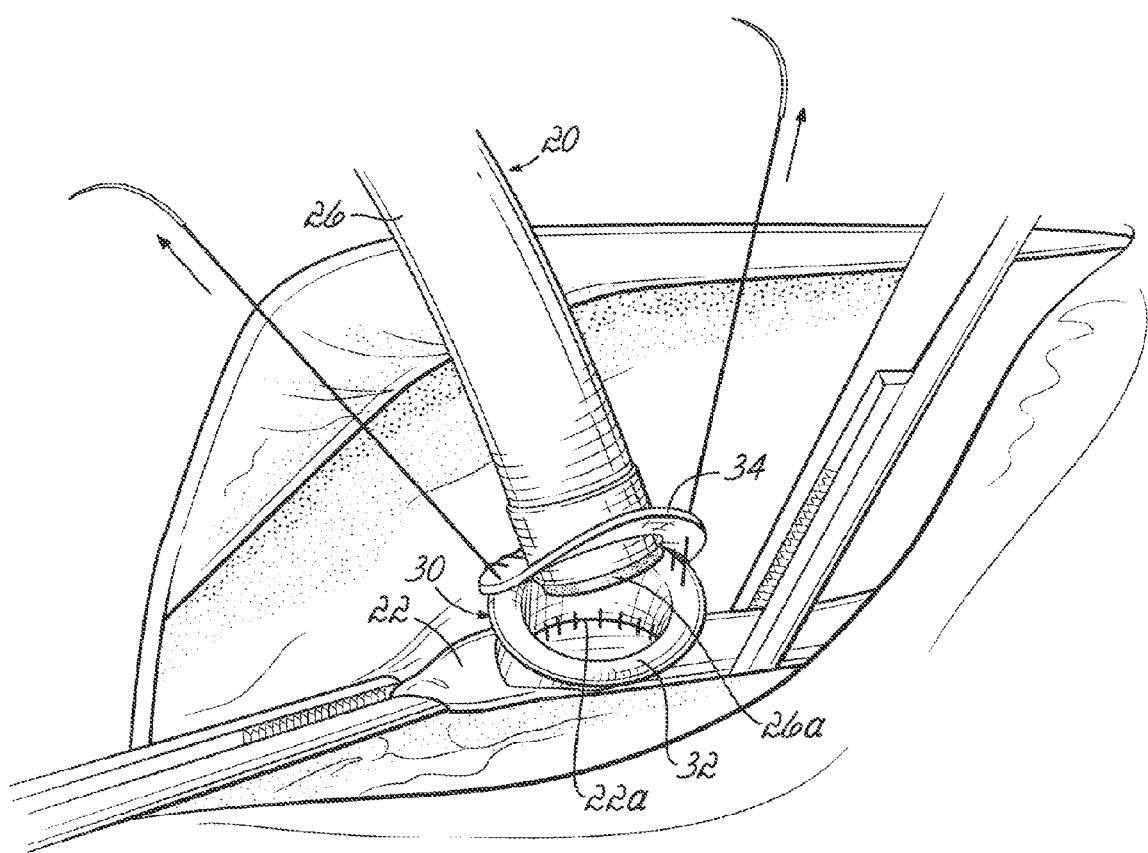
FIG. 4 is a perspective view similar to FIGS. 2 and 3, and further illustrating a blood flow conduit being attached to the graft element.

FIG. 4 shows how a junction between the silicone material portion 26 of the conduit 20 and the graft element 30 is recreated when a rim or flange 34 of sewing material or graft material, for example, of the conduit portion 26 is affixed to the flange 32 on the element 30 previously anastomosed to the artery 22.

Figure 5:
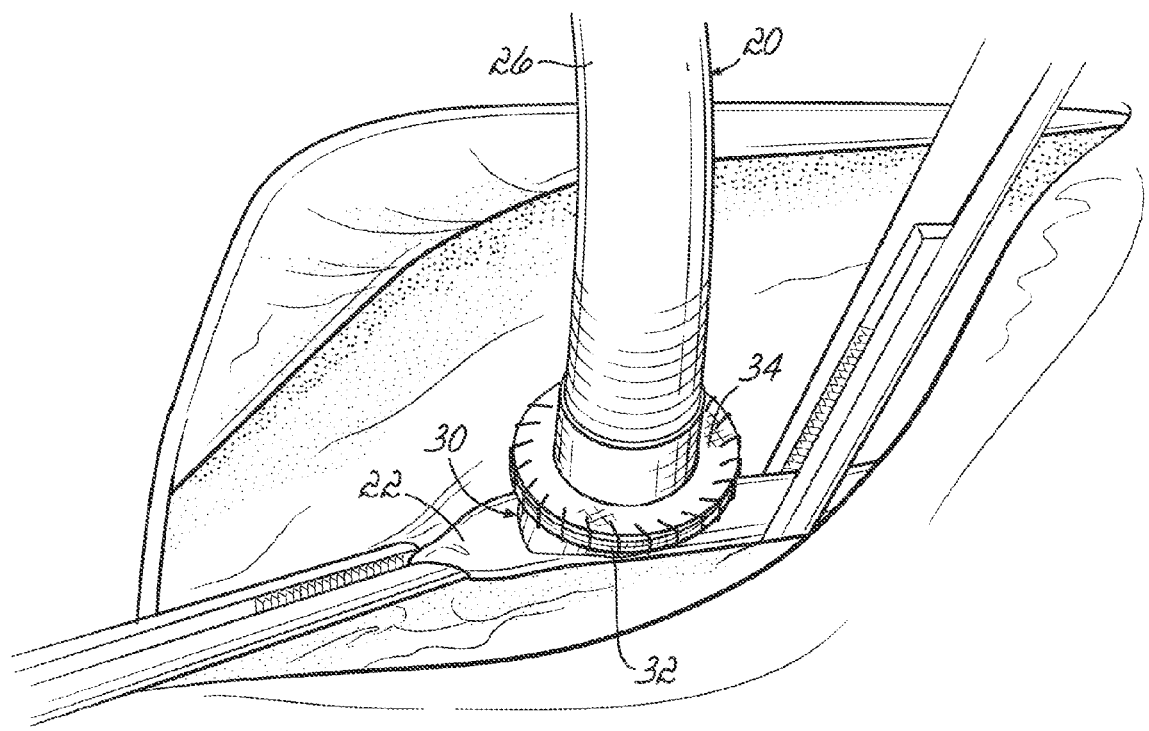
FIG. 5 is a perspective view similar to FIGS. 2 through 4, and further illustrating the blood flow conduit attached to the graft element.

FIG. 5 shows how the two flanges 32, 34 are sewn together. This is a very easy anastomosis to perform.

It will be appreciated that these flanges 32, 34 could be joined not just by sutures but by staples, clips, glues, clamps etc.

Figure 6A:
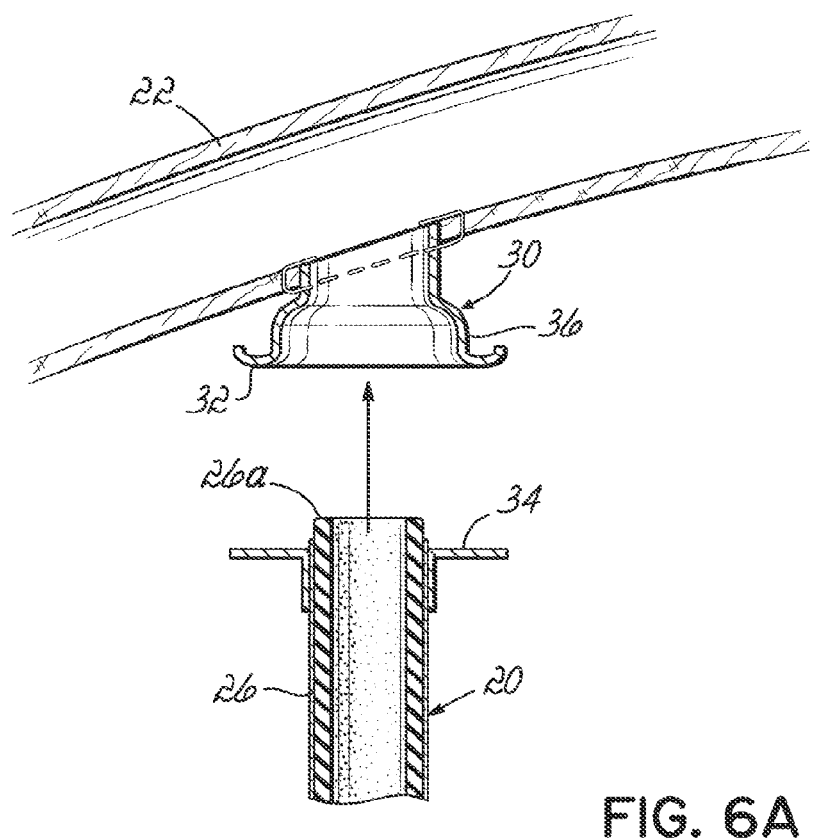
FIG. 6A is a cross-sectional view illustrating the blood flow conduit being attached to the graft element.

FIG. 6A shows a side cross sectional view of the two flanges 32, 34 coming together.

Figure 6B:
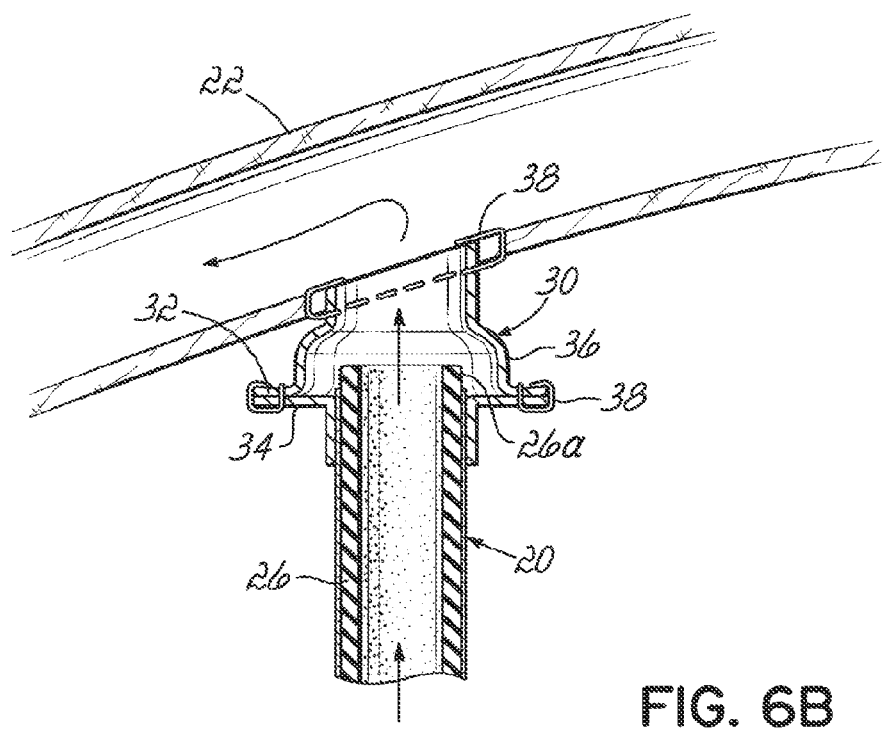
FIG. 6B is a cross-sectional view illustrating the blood flow conduit attached to the graft element.

FIG. 6B shows how the bubble or enlarged connector 30 does not have to be flat—it could be beveled. Also the connector 30 does not have to be a generally spherical bubble as shown elsewhere herein. The key is only that the enlarged area keeps the silicone and graft surfaces (that is, smooth and rough flow surfaces) from direct contact at their junction during use.

The bubble or enlarged area 36 is quite useful as it allows the graft to move or "swivel" inside the bubble 36 and still not contact the wall of the bubble 36.

FIG. 6B also shows clips or staples 38 attaching the connector 30 to the artery 22 and attaching the flanges 32, 34 together.

The conduit portion 26 does not have to be entirely silicone. It could have any inner core that presents a compatible surface to the exposed blood. For example, the inside could be metal, have a metal spiral reinforcement, etc. It could also have graft material inside like ePTFE or other polyester.

The smooth surface does not have to be silicone. This is used as representative of a smooth surface. The surface could be a metal or plastic (such as in the pump connection shown in FIGS. 10A and 10B.)

Figure 7:
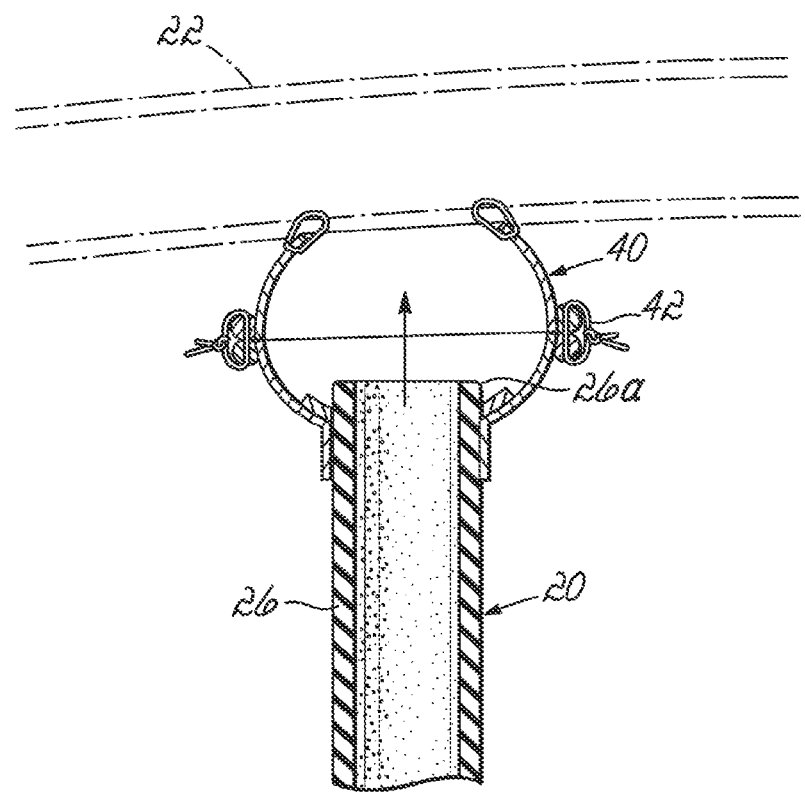
FIG. 7 is a cross-sectional view of a graft element attached to a blood flow conduit and an artery.

FIG. 7 shows a bubble or enlarged area 40 constructed by "splitting" the bubble in the middle of the hemisphere. It could be equally possible to form the junction 42 anywhere in this arrangement; the location at the hemisphere is merely an example.

Alternatively, a more complete bubble could be created and the silicone cannula could be slipped into a defect at the end to perform the same function.

It should be noted that the terms used are basically smooth (silicone, plastics, metals) and rough or textured surfaces (Dacron, Teflon, ePTFE). It is also possible to have a tightly woven or knitted material that is typically called a textile, but could function as a smooth surface.

Also, it is possible to create a tightly woven polyester that behaves like a smooth surface. It could be possible to bring a tightly woven sewable graft into direct contact with a silicone surface without an intervening "bubble" or step.

It may also be important to prevent these conduits from collapsing as they can be located below the skin and could be crushed by a patient lying on them. Reinforcement of the conduits with plastic or wire spirals or rings can be used here. In addition, extra thicknesses of polymer or plastic could be added make them stronger.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features discussed herein may be used alone or in any combination depending on the needs and preferences of the user. This has been a description of illustrative aspects and embodiments the present invention, along with the preferred methods of practicing the present invention as currently known.

What is claimed is:

1. A blood flow conduit, comprising:
   a first conduit portion defining a first portion of a lumen, including a tip portion; and
   a second conduit portion defining a second portion of a lumen, the second conduit portion including an extension and an enlarged area,
   wherein:
   the extension and enlarged area are formed of graft material;
   a cross-sectional area of the enlarged area is greater than a cross-sectional area of the extension; and
   the tip portion extends at least partially into the enlarged area in a manner designed to prevent contact between the tip portion and an inner wall of the enlarged area as blood flows through the lumen.

2. The blood flow conduit of claim 1, wherein the tip portion includes an inner wall with a surface roughness less than a surface roughness of the inner wall of the enlarged area.

3. The blood flow conduit of claim 2, wherein the tip portion is formed from at least one material selected from the group consisting of metals or polymers, and the enlarged area is formed from a material that promotes tissue or cell ingrowth.

4. The blood flow conduit of claim 2, wherein the tip portion is formed from at least partially from silicone, and the enlarged area is formed from a fabric or textile.

5. The blood flow conduit of claim 1, wherein the enlarged area is formed in at least two pieces adapted to be affixed together during a surgical procedure.

6. The blood flow conduit of claim 1, wherein the tip portion is part of a blood pump.

7. The blood flow conduit of claim 1, wherein the first and second conduit portions are configured to be affixed together during a surgical procedure.

8. The blood flow conduit of claim 1, wherein the first and second conduit portions are configured to be affixed together and to a pump during a surgical procedure.

9. The blood flow conduit of claim 1, further comprising a washer affixed around the tip portion.

10. A blood flow assist system, comprising:
    a blood pump; and
    a blood flow conduit as set forth in claim 1.

* * * * *